| (12) | United States Patent | (10) Patent No.: | US 8,435,972 B2 |
|---|---|---|---|
| | Stein et al. | (45) Date of Patent: | May 7, 2013 |

(54) METHOD FOR THE TREATMENT OF CENTRAL NERVOUS SYSTEM CANCERS AND COMPOSITIONS RELATED THERETO

(75) Inventors: Donald G. Stein, Atlanta, GA (US); Iqbal Sayeed, Atlanta, GA (US); Fahim Atif, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/222,021

(22) Filed: Aug. 31, 2011

(65) Prior Publication Data

US 2012/0058978 A1 Mar. 8, 2012

Related U.S. Application Data

(60) Provisional application No. 61/379,472, filed on Sep. 2, 2010.

(51) Int. Cl.
*A61K 31/56* (2006.01)

(52) U.S. Cl.
USPC .......................................................... 514/177

(58) Field of Classification Search .................. None
See application file for complete search history.

(56) References Cited

U.S. PATENT DOCUMENTS

2009/0068257 A1* 3/2009 Leunis et al. ................. 424/450

FOREIGN PATENT DOCUMENTS

| WO | 9507699 A1 | 3/1995 |
| WO | 9959595 A1 | 11/1999 |
| WO | 2009108804 A2 | 9/2009 |

OTHER PUBLICATIONS

Inoue et al. Progesterone production and actions in the human central nervous system and neurogenic tumors. The Journal of Clinical Endocrinology & Metabolism, 87(11): 5325-5331.*
Veal et al. Pharmacokinetics of carboplatin and etoposide in infant neuroblastoma patients. Cancer Chemother. Pharmacol., 2010, 65: 1057-1066.*
Agis-Balboa et al., (2006), "Characterization of brain neurons that express enzymes mediating neurosteroid biosynthesis.", Proceedings of the National Academy of Sciences, 103(39): 14602-14607.
Badwe et al., (2011), "Single-Injection Depot Progesterone Before Surgery and Survival in Women With Operable Breast Cancer: A Randomized Controlled Trial.", Journal of Clinical Oncology, 29(21): 2845-2851.
Balant et al., (1990), "Prodrugs for the improvement of drug absorption via different routes of administration.", European Journal of Drug Metabolism and Pharmacokinetics, 15(2): 143-153.
Balimane et al., (1999), "Involvement of multiple transporters in the oral absorption of nucleoside analogues." Advanced Drug Delivery Reviews, 39(1-3): 183-209.
Boman et al., (1993), "The influence of progesterone and androgens on the growth of endometrial carcinoma.", Cancer, 71(11): 3565-3569.
Browne, T., (1997), "Fosphenytoin (Cerebyx).", Clinical Neuropharmacology 20(1): 1-12.
Bu et al., (1997), "Progesterone induces apoptosis and up-regulation of p53 expression in human ovarian carcinoma cell lines.", Cancer, 79(10): 1944-1950.
Cowan et al., (1981), "Breast Cancer Incidence in Women With a History of Progesterone Deficiency.", American Journal of Epidemiology, 114(2): 209-217.
Fleisher et al., (1996), "Improved oral drug delivery: solubility limitations overcome by the use of prodrugs.", Advanced Drug Delivery Reviews, 19(2): 115-130.
Fleisher et al., (1985), "Design of prodrugs for improved gastrointestinal absorption by intestinal enzyme targeting.", Methods in Enzymology, Kenneth et al, Academic Press. vol. 112: 360-381.
Foidart et al., (1998), "Estradiol and Progesterone Regulate the Proliferation of Human Breast Epithelial Cells.", Fertility and Sterility, 69(5): 963-969.
Formby et al., (1999), "Bcl-2, survivin and variant CD44 v7-v10 are downregulated and p53 is upregulated in breast cancer cells by progesterone: Inhibition of cell growth and induction of apoptosis.", Molecular and Cellular Biochemistry, 202(1): 53-61.
Han et al., (2000), "Targeted prodrug design to optimize drug delivery.", The AAPS Journal, 2(1): 48-58.
Horita et al., (2001), "Progesterone induces apoptosis in malignant mesothelioma cells.", Anticancer Res, 21(6A): 3871-3874.
Inoue et al., (2002), "Progesterone Production and Actions in the Human Central Nervous System and Neurogenic Tumors.", Journal of Clinical Endocrinology & Metabolism, 87(11): 5325-5331.
Lambert, D., (2000), "Rationale and applications of lipids as prodrug carriers.", European Journal of Pharmaceutical Sciences, 11, Supplement 2(0): S15-S27.
Lorenz et al., (2009), "Combined 17β-Oestradiol and Progesterone Treatment Prevents Neuronal Cell Injury in Cortical but not Midbrain Neurones or Neuroblastoma Cells.", Journal of Neuroendocrinology, 21(10): 841-849.
MacNevin et al., (2009), "Development and Screening of Water-Soluble Analogues of Progesterone and Allopregnanolone in Models of Brain Injury.", Journal of Medicinal Chemistry, 52(19): 6012-6023.
Maggi et al., (1998), "Effects and Metabolism of Steroid Hormones in Human Neuroblastoma Cells.", Steroids, 63(5-6): 257-262.
Maris et al., (1999), "Molecular Biology of Neuroblastoma.", Journal of Clinical Oncology, 17(7): 2264.
Mizen et al., (2002),"The Use of Esters as Prodrugs for Oral Delivery of β-Lactam Antibiotics Integration of Pharmaceutical Discovery and Development.", Pharmaceutical Biotechnology, 11: 345-365.
Pauletti et al., (1997), "Improvement of oral peptide bioavailability: Peptidomimetics and prodrug strategies.", Advanced Drug Delivery Reviews, 27(2-3): 235-256.
Ries et al., (2005), "SEER Cancer Statistics Review 1975-2003", National Cancer Institute, Bethesda, MD, http://seer.cancer.gov/csr/1975_2003/.

(Continued)

*Primary Examiner* — Anna Pagonakis
(74) *Attorney, Agent, or Firm* — Emory Patent Group; James C. Mason; Susanne Hollinger

(57) ABSTRACT

Use of compounds disclosed herein, typically progesterone or analog or derivative thereof, in the treatment of central nervous system cancers, specifically neuroblastoma and glioblastoma is provided. The treatment offers a reduced toxicity as compared to the currently available chemotherapeutic agents. The progesterone may be administered alone or in combination with, or in conjunction with other therapeutic agents.

6 Claims, 16 Drawing Sheets

OTHER PUBLICATIONS

Robel et al., (1994), "Neurosteroids: Biosynthesis and function.", Trends in Endocrinology & Metabolism, 5(1): 1-8.

Sadzuka, Y., (2000), "Effective Prodrug Liposome and Conversion to Active Metabolite.", Current Drug Metabolism, 1(1): 31-48.

Saijo et al., (2003), "Strategy for the development of novel anticancer drugs.", Cancer Chemother Pharmacol, 52: S97-S101.

Wagner et al., (2009), "New therapeutic targets for the treatment of high-risk neuroblastoma.", Journal of Cellular Biochemistry, 107(1): 46-57.

Wang et al., "Prodrug approaches to the improved delivery of peptide drugs.", Curr. Pharm. Design, 5(4):265-287.

Weinstein et al., (2003), "Advances in the Diagnosis and Treatment of Neuroblastoma.", The Oncologist, 8(3): 278-292.

Wright et al., (2007), "ProTECT: A Randomized Clinical Trial of Progesterone for Acute Traumatic Brain Injury.", Annals of Emergency Medicine, 49(4): 391-402.e392.

* cited by examiner

Vehicle

Progesterone (50 mg/kg)

Progesterone (100 mg/kg)

METHOD FOR THE TREATMENT OF CENTRAL NERVOUS SYSTEM CANCERS AND COMPOSITIONS RELATED THERETO

This application Claims priority to U.S. Provisional Patent Application No. 61/379,472 filed 2 Sep. 2010, hereby incorporated by reference.

FIELD

This disclosure relates to the use of certain compounds and steroid, and in particular progesterone, analogues and derivatives thereof, for the treatment of central nervous system cancer, in particular neuroblastoma and glioblastoma.

BACKGROUND

Neuroblastoma is a cancer of specialized nerve cells that are involved in the development of the nervous system and other tissues. It is the most common extra-cranial solid tumor of childhood and one of the deadliest neoplasms in childhood, accounting for 15% of childhood deaths. Approximately 96% of the cases occur before the age of 10 years.

The disease commonly originates in the adrenal medulla and others sites of sympathetic nervous tissue. The most common occurrence of neuroblastoma is in the abdomen (near the adrenal gland) but it can also be found in the chest, neck, pelvis, or other sites. By the time it is diagnosed, the cancer has usually metastasized to the lymph nodes, liver, lungs, bone and bone marrow. Most neuroblastoma patients have widespread occurrence at diagnosis. Neuroblastomas may compress the spinal cord, causing paralysis.

Neuroblastoma tumors grow aggressively, metastasize, induce angiogenesis and remain resistant to multimodal therapy, demonstrating the need for novel therapeutic strategies that address efficient inhibition of cancer cells and eradication of any remaining refractory microscopic disease. Although high risk patients receive an aggressive regimen of combination chemotherapy, the cancer frequently recurs and up to 80% of patients die of disseminated disease. New and effective cancer treatments are constantly being sought. There is also an urgent need to improve the outcome for patients with the disease, with an increased emphasis for development of new drugs that are highly effective in eliminating aggressive cancer cells while also having insignificant toxicity towards normal cells.

Typical therapies include radiation and drug treatments; unfortunately many are toxic and harmful to normal cells. Although state of the art chemotherapy regimens have been established, the survival benefits still remain negligible (Saijo et al., 2003, *Cancer Chemother Pharmacol.*, 52 Suppl 1:S97-101). For neuroblastoma in particular, there are a number of ongoing Phase III and Phase IV trials for new strategies to treat the disease, yet a safe and effective drug that avoids adverse effects has not yet been found. The cost of the cure can be quite high as the surviving children are exposed to additional health problems because of the long term toxicities of the treatment (Wagner and Danks, 2009, *J Cell Biochem*, 107:46-53). Certain steroids, in particular progesterone, have been proposed as useful in treatment of certain cancers. For example, progesterone has been proposed as having apoptotic effects against certain hormonally regulated cancer cells, such as from breast, endometrial and ovarian tumors. Natural progesterone has been shown to inhibit the proliferation of breast epithelial cells (Foidart et al., 1998, *Fertility and Sterility*, 69:963-969) and high natural progesterone levels similar to those seen during the third trimester of pregnancy exhibited a strong anti-proliferative effect on at least two breast cancer cells lines (Formby and Wiley, 1999, *Mol Cell Biochem*, 202: 53-61; WO99/59595).

It has also been proposed that progesterone deficiency is linked with the occurrence of breast cell carcinoma, for example in women with endogenous progesterone deficiency who have a heightened risk of premenopausal breast cancer occurrence and death (Cowan et al., 1981, *Am J Epidemiol*, 114:209-217). Boman et al. found that endogenous progesterone plays a role in the control of the breast tumor's proliferation activity (Boman et al., 1993, *Cancer*, 71:3564-9), and it was also recently shown that a single injection of depot progesterone prior to breast cancer therapy reduced mortality by more than 35% in over 1000 women 65 months after diagnosis and treatment (Badwe et al., 2009, $32^{nd}$ San Antonio breast Cancer Symposium, December 9-13, TX USA).

In addition to breast cancer, endometrial and ovarian cancer have been linked to progesterone therapy. For example, PCT Publication WO 95/07699 asserts that relatively low levels of serum progesterone, 1 to 6 ng/ml, may be used to prevent endometrial cancer. It has also been shown that progesterone replacement therapy reduces the risk of developing ovarian carcinoma in post menopausal women and is also useful for treating some types of ovarian tumors (Bu et al., 1997, *Cancer*, 79:1944-1950).

Progesterone therapy has also been proposed in the treatment or prevention of ischemic damage in the central nervous system. Beneficial effects of progesterone have been demonstrated in experimental models of traumatic brain injury, and it has been shown to have a very high safety profile and limited side effects in clinical testing as a treatment for brain injury (Wright et al., 2007, *Annals of Emergency Medicine*, 49:391-402).

In their study of the use of estradiol and progesterone acting for the prevention of neuronal damage induced by ischaemia in the central nervous system, Lorenz et al. found that the combined and single steroid treatment offered no cell protection to neuroblastoma cells (Lorenz et al., 2009, *J Neuroendodrinol*, 21:841-9). Indeed, Maggi et al. showed a significant decrease in cell viability of neuroblastoma cells at 10 µM of progesterone (Maggi et al., 1998, *Steroids*, 63:257-262). Progesterone administration has been shown to suppress cell proliferation and induce apoptosis in malignant mesothelioma cells (Horita et al., 2001, *Anticancer Res.*, 21:3871-3874). Progesterone has been proposed as potentially acting through progesterone receptor A (Inoue et al., 2002, *J Clin Endocrinol Metab.*, 87:5325-5331), although this was not demonstrated.

There remains a need for improved therapy of nervous system tumors such as neuroblastoma that has reduced toxicity over existing treatments. The object of this disclosure is to provide compounds, methods and compositions for treatment or prophylaxis of central nervous system tumors, particularly neuroblastoma and glioblastoma.

SUMMARY

This disclosure provides a new therapy for certain central nervous system tumors. It has been surprisingly found that certain steroids are effective in reducing central nervous system (CNS) tumor size and growth. In particular, the naturally occurring steroid progesterone, analogues and derivatives thereof, can be useful to reduce CNS tumors.

In one embodiment a method of treatment of CNS tumors is provided including administering a neuroactive steroid to a subject in need thereof. In certain embodiments, the CNS tumor is a neuroblastoma or a glioblastoma. The steroid can be any neuroactive steroid, but in particular embodiments is progesterone or an analogue or derivative thereof. In certain embodiments, administration of the steroid can induce cell death in human neuroblastoma and glioblastoma cells, while having no detrimental effect on primary cortical neurons. The administration of the steroid and in particular the administration of progesterone or an analogue or derivative thereof can reduce the rate of daily tumor growth in the subject. In other embodiments, the steroid administration can reduce the size of an existing tumor in a subject.

Typically the subject has been diagnosed as having a CNS tumor. Tumors of the CNS include, but are not limited to, cancers such as neuroblastoma and glioblastoma. Subjects can be any mammal, and are preferably human subjects. The subjects can be of any age, ranging from new born babies to fully grown adults, however is typically under twenty-one years old. In certain embodiments, the subject is not an adult, and typically can range in age from one to twenty-one years, or more typically less than eighteen, or even more typically less than thirteen years old. Typically, the subject has not completed puberty. In certain embodiments, the progesterone is administered to a subject not suffering from a hormone-related disorder, and in particular is typically not suffering from a breast, endometrial or ovarian cancer.

In one embodiment, treatment of the CNS tumor is provided by a single dose of the steroid, while in another embodiment the treatment is provided by repeated exposure to the steroid. In certain embodiments, the steroid, and typically progesterone or an analogue or derivative thereof, is administered at least one time per day for at least two, at least three, at least four, at least five, at least six, at least seven or more days. The steroid can also be administered less than once a day, over the course of at least one week, or at least two weeks, or at least three weeks, or one month or more.

The steroid may be used in conjunction with one or more additional compounds, in the treatment of the inhibition of CNS tumors. In some embodiments, the method of administration of the steroid is oral. In other embodiments, the steroid is administered by injection, such as, through a peritumoral injection.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

DETAILED DESCRIPTION OF THE DISCLOSURE

Figure 1A:
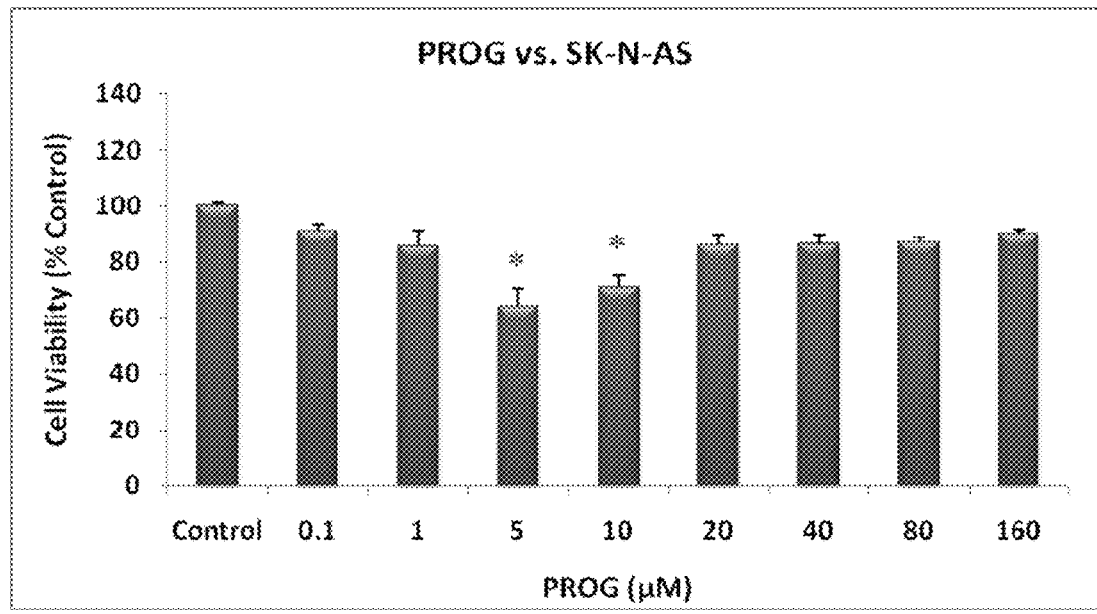
FIG. 1 shows the effect of progesterone in single exposure on the viability of [A] human neuroblastoma (SK-N-AS) cells; [B] PC-12 cells; and [C] primary cortical neurons (MTT assay). Data were evaluated by analysis of variance (ANOVA) followed by Dunnett test for individual comparisons. The significance of the results were set at P<0.05 when compared to controls. Values were expressed as means±SD of three experiments.
Figure 1B:
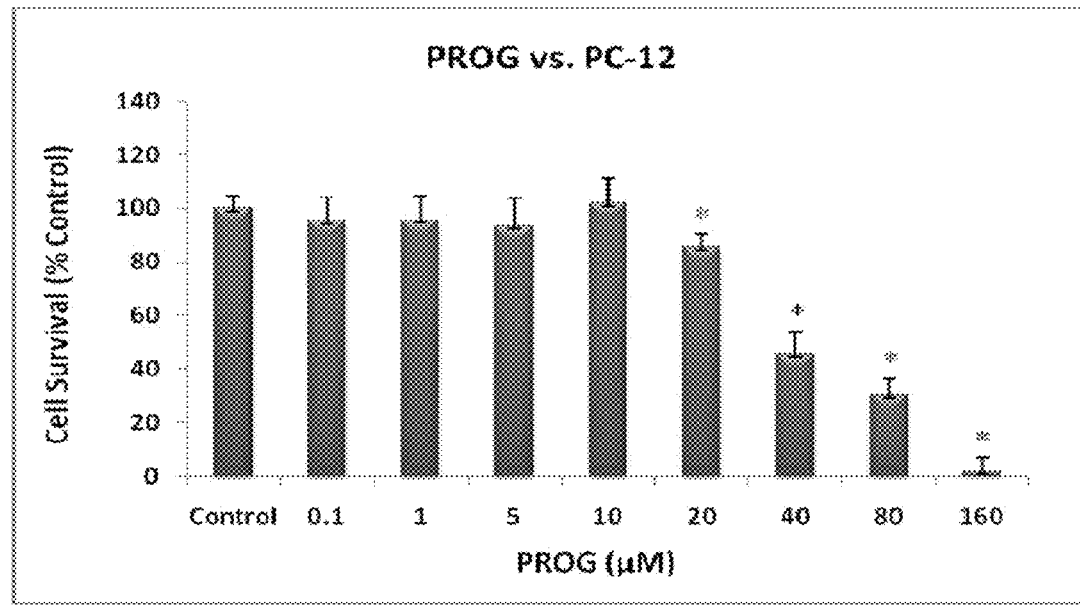

Embodiments of disclosure now will be described more fully hereinafter with reference to the accompanying drawings, in which some, but not all embodiments of the disclosures are shown. Indeed, these disclosures may be embodied in many different forms and should not be construed as limited to the embodiments set forth herein; rather, these embodiments are provided so that this disclosure will satisfy applicable legal requirements.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Definitions

As used herein, "analogue" refers to a chemical compound that is structurally similar to a parent compound, but differs slightly in composition (e.g., one atom or functional group is different, added, or removed). The analogue may or may not have different chemical or physical properties than the original compound and may or may not have improved biological and/or chemical activity. For example, the analogue may be more hydrophilic or it may have altered reactivity as compared to the parent compound. The analogue may mimic the chemical and/or biologically activity of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med.

Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.*, 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.*, 72(3): 324-325; Han, H. K. et al. (2000). Targeted prodrug design to optimize drug delivery, *AAPS PharmSci.*, 2(1): E6; Sadzuka Y. (2000). Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl 2:S15-27; Wang, W. et al. (1999) Prodrug approaches to the improved delivery of peptide drugs. *Curr. Pharm. Des.*, 5(4):265-87.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment," and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies. "Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths; (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of the compounds described herein or pharmaceutically acceptable salts thereof, with other chemical components, such as physiologically acceptable carriers and excipients. One purpose of a pharmaceutical composition is to facilitate administration of a compound to a subject.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "including", "such as", "for example" and the like are intended to refer to exemplary embodiments and not to limit the scope of the present disclosure.

Compounds

The disclosure provides methods of treatment or prophylaxis of certain tumors including the use of a neuroactive steroid. Neuroactive steroids are active on the central or peripheral nervous system. Certain of these compounds can rapidly alter neuronal excitability through interaction with neurotransmitter-gated ion channels, and also exert effects on gene expression via intracellular steroid hormone receptors. Typically, neuroactive steroids have been proposed as having clinical application in sedation, treatment of epilepsy and traumatic brain injury.

Neurosteroids are synthesized in the central and peripheral nervous system, especially in myelinating glial cells, from cholesterol or steroidal precursors imported from peripheral sources (see eg. Agís-Balboa, et al. (2006). *Proc. Natl. Acad. Sci. U.S.A.* 103 (39): 14602-7). They include 3β-hydroxy-Δ5 derivatives, such as pregnenolone and dehydroepiandrosterone (DHEA), their sulfates, and reduced metabolites such as the tetrahydroderivative of progesterone 3α-hydroxy-5α-pregnane-20-one (3α,5α-THPROG), the 3α-hydroxy ring A-reduced pregnane steroids allopregnanolone and tetrahydrodeoxycorticosterone, alphaxolone, alphadolone, hydroxydione and minaxolone, ganaxolone, and progesterone itself.

Progesterone, also known as P4 from its chemical name pregn-4-ene-3,20-dione, is a C-21 steroid hormone involved in the female menstrual cycle, pregnancy (supports gestation) and embryogenesis of humans and other species.

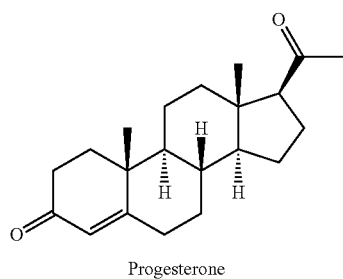

Progesterone

Progesterone belongs to a class of hormones called progestogens, and is the major naturally occurring human progestogen. Progesterone is produced in the ovaries (specifically after ovulation in the corpus luteum), the adrenal glands (near the kidney), and, during pregnancy in the placenta. Progesterone is also stored in adipose (fat) tissue. Since progesterone, among other steroids, is accumulated in the brain, independently (at least in part) of the steroidogenic gland contribution, and its presence can be related to steroid biosynthetic pathways in the brain, it is designated as a neurosteroid (Robel and Baulieu, 1995, *Crit. Rev Neurobiol.*, 9:383-394).

Progesterone has also been postulated to be involved in the biological behavior of various human neurogenic tumors via progesterone receptors A and B (PR-A and PR-B). These findings suggest that progesterone is locally synthesized and exerts its actions through PR in the human central nervous system, and that progesterone may be involved in regulation of the growth and development of neurogenic tumors via PR, especially in the inhibition of tumor cell proliferation via PR-A (Inoue et al., 2002, *J Clin Endocrinol Metab.*, 87:5325-5331,).

Other compounds contemplated in methods described herein include those described in PCT Publication WO 2009/108804, hereby incorporated by reference, such as compounds of Formula I:

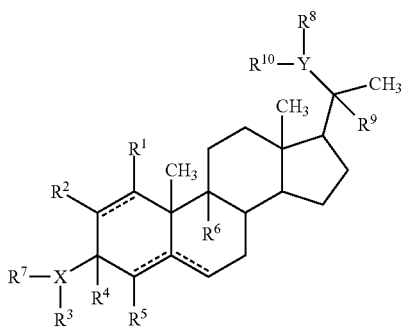

or salts thereof, wherein X is O, N or S;
Y is O, N or S;
$R^1$, $R^2$, $R^5$ and $R^6$ are independently hydrogen, alkyl, halogen, hydroxyl, cyclo alkyl, cycloalkenyl, alkenyl, alkynyl, aryl, alkylaryl, arylalkyl, heterocyclic, hetero aryl, amino, thiol, alkoxy, sulfide, nitro, cyano, azide, sulfonyl, acyl, carboxyl, an ester, an amide, carbamate, carbonate, an amino acid residue or a carbohydrate;
$R^4$ is hydrogen or alkyl; $R^4$ together with $R^3$ and X forms an optionally substituted 5-6 membered heterocyclic or heteroaryl ring containing 1-4 nitrogen, oxygen or sulfur atoms; or $R^4$ and $R^7$ together form a double bond;
$R^3$ is hydrogen, optionally substituted acyl, a residue of an amino acid, a carbohydrate, monophosphate, diphosphate, triphosphate, —$OR^{11}$, —$NR^{11}R^{12}$; —$C(O)R^{11}$, where R' is alkyl, aryl, arylalkyl, $OR^1$, $NR^1R^2$ or the residue of an amino acid; $R^3$ together with X and $R^4$ forms an optionally substituted 5-6 membered heterocyclic or heteroaryl ring containing 1-4 nitrogen, oxygen or sulfur atoms, or $R^3$ is absent;
$R^7$ is hydrogen or is absent, or $R^7$ together with $R^4$ forms a double bond;
$R^8$ is hydrogen, optionally substituted acyl, a residue of an amino acid, a carbohydrate, monophosphate, diphosphate, triphosphate, —$OR^{11}$, —$NR^{11}R^{12}$; —$C(O)R'$, where R' is alkyl, aryl, arylalkyl, $OR^1$, $NR^1R^2$ or the residue of an amino acid; $R^8$ together with $R^9$ and Y forms an optionally substituted 5-6 membered heterocyclic or heteroaryl ring containing 1-4 nitrogen, oxygen or sulfur atoms, or $R^8$ absent;
$R^9$ is hydrogen or alkyl; $R^9$ together with Y and $R^8$ forms an optionally substituted 5-6 membered heterocyclic or heteroaryl ring containing 1-4 nitrogen, oxygen or sulfur atoms; or $R^9$ and $R^{10}$ together form a double bond;
$R^{10}$ is hydrogen or is absent, or $R^{10}$ together with $R^9$ forms a double bond;
$R^{11}$ is hydrogen, optionally substituted alkyl, hydroxyalkyl, amino alkyl, monophosphate, diphosphate, triphosphate, the residue of an amino acid, a carbohydrate, an optionally substituted ester, or —C(O)R', where R' is alkyl, aryl, arylalkyl, $OR^1$, $NR^1R^2$ or the residue of an amino acid;
$R^{12}$ is hydrogen or alkyl; and the dotted line indicates the presence of either a single bond or a double bond, wherein the valencies of a single bond are completed by hydrogens.

Methods of Treatment

In one embodiment a method of treatment of CNS tumors is provided including administering a compounds disclosed herein to a subject in need thereof. The compound can be any neuroactive steroid, but in particular embodiments is progesterone or an analogue or derivative thereof. In certain embodiments, administration of the steroid can induce cell death in human neuroblastoma and glioblastoma cells, while having no detrimental effect on primary cortical neurons. The administration of the compound and in particular the administration of progesterone or an analogue or derivative thereof can reduce the rate of daily tumor growth in the subject.

Cancer (medical term: malignant neoplasm) is a class of diseases in which a group of cells display uncontrolled growth i.e. division beyond the normal limits, invasion (intrusion on and destruction of adjacent tissues), and sometimes metastasis, which is the spread to other locations in the body via lymph or blood. These three malignant properties of cancers differentiate them from benign tumors, which are self-limited, and do not invade or metastasize.

Most cancers form a tumor but some, like leukemia, do not. According to the SEER Cancer Statistics Review 1975-2003 (National Cancer Institute), close to a million and a half persons develop new cancers each year and over a half a million die from cancer. Cancer is second only to accidents as a cause of death in children 1 to 14 years old. It causes 10.5% of all deaths. The CNS is among the three leading sites of cancer mortality in the first three decades of life.

Neuroblastoma is the most common heterogenous and malignant tumor of early childhood. It is a solid cancerous tumor that begins in nerve tissues in the neck, chest, abdomen or pelvis but usually originates in the abdomen in adrenal gland tissue. By the time it is diagnosed, the cancer has usually metastasized to the lymph nodes, liver, lungs, bones and bone marrow. Two thirds of children with neuroblastoma are diagnosed when they are younger than 5 years. While frequently present at birth, neuroblastoma is usually not detected until later. In rare cases, neuroblastoma can be detected before birth by fetal ultrasound.

There are approximately 500-1000 new cases of neuroblastoma in the U.S. each year (Weinstein et al., 2003, *Oncologist*, 8:278-292). Neuroblastoma accounts for 7 to 10% of all childhood cancers and it is the most common cancer diagnosed during infancy. The hallmark of neuroblastoma is heterogeneity: some tumors regress spontaneously, whereas others differentiate into benign ganglioneuromas. Unfortunately the majority of patients over 1 year of age develop locally aggressive and/or metastatic fatal disease.

Neuroblastoma is derived from the neural crest and is characterized by a marked clinical heterogeneity (aggressive, unremitting growth to spontaneous remission). As classified by International Neuroblastoma Staging System (INSS) there are six stages of neuroblastoma: Stage 1 (localized resectable), Stage 2A and 2B (localized unresectable or ipsilateral lymph node involvement), Stage 3 (regional, unresectable and crossing the midline), Stage 4 (disseminated) and Stage 4S (localized with limited spread; less than one year of age) referred to as "special" neuroblastoma.

Presenting signs and symptoms of children with neuroblastoma reflect both the location of the primary tumor and the extent of the disease. Patients with localized disease are often asymptomatic, while children with metastatic disease typically appear ill at presentation with systemic symptoms, including fever and bone pain. About 40% of children with neuroblastoma respond to radiation and single agent chemotherapy. These patients are considered the 'low-risk' group characterized by the lack of N-myc amplification. Patients with metastatic neuroblastoma are considered the 'high-risk' group. Their tumors generally demonstrate amplification of the N-myc proto-oncogene, contain poorly differentiated cells, and respond poorly to conventional chemo- and radiotherapies (Maris and Matthay, 1999, *J Clin Oncol.*, 17:2264-2279).

At the time of diagnosis, approximately 50% of infants and 70% of older neuroblastoma patients have disseminated disease spread beyond the primary site to the lymph nodes, bone marrow, and liver.

Treatment methods currently available are used either singly or in combination depending on the location, biological characteristics of the cancer cells, stage and risk group to which the patient belongs to (low, intermediate and high risk). These include surgery, radiation therapy, chemotherapy and bone marrow or stem cell transplantation. Low-risk neuroblastoma patients require minimal therapy; excellent outcome is also seen in patients with stages 2A and 2B disease. Intermediate-risk patients with favorable biology tumors are treated with a short course of chemotherapy (four cycles), while intermediate-risk patients with unfavorable biology receive a longer course of chemotherapy (eight cycles). Current treatment for high risk patients includes surgery and high dose chemotherapy with autologous stem cell rescue.

The side effects of chemotherapy depend on the individual and the dose used, but can include fatigue, risk of infection, nausea and vomiting, loss of appetite, and diarrhea. These side effects usually go away once treatment is finished. The severity of the side effects depends on the type and amount of the drug being given and the length of time the child receives the drug.

However, in spite of aggressive therapy the disease relapses, and up to 80% of patients die of disseminated disease. Eradication of refractory microscopic disease remains one of the most significant challenges in the treatment of high-risk neuroblastoma. Hence, developing new therapeutic modalities is vital in order to improve the outcome for patients with neuroblastoma.

Treatment options for neuroblastoma depend on age at diagnosis, tumor location, stage of disease, regional lymph node involvement and the tumor biology. Generally four types of treatment are involved, alone or in combination, and include surgery to remove the tumor, radiation therapy, chemotherapy and bone marrow transplantation. The most common therapies include radiation and drug treatments; unfortunately many are toxic and harmful to normal cells. They include the use of cytotoxic agents (topotecan, a topoisomerase I inhibitor, cisplatin, doxorubicin and cyclophosphamides, either alone or in combination) retinoids (13-cis-RA, all-trans-RA and fenretinide), immunotherapy (anti-GD2 antibodies), cytokines (GM-CSF and IL2) radioiodinated meta-iodobenzylguanidine (to target delivery of radiotherapy).

Unfortunately, survival for high risk children has improved only modestly during the past 20 years. This improvement is thought to be due to the intensification of induction chemotherapy, megatherapy consolidation, and improved support care. Despite intensive multimodality treatment, more than 50% of children with high-risk disease will relapse due to drug-resistant residual disease. Despite progress in chemotherapy, many chemical agents become ineffective and may cause serious side effects due to toxicity of high dosages required to prevent cancer growth.

Even when the majority of the cells within the tumor are killed, a small number of unaffected cells may be able to reestablish the aberrant pattern of proliferation. Tumor cells may simply develop resistance to chemical and radiation treatment, leading to recurrence of chemo- and/or radio-resistant cancers because the resistant cells maintain their ability to proliferate indefinitely. Resistance may also develop because administration of chemotherapeutic agents for the treatment of tumors is restricted by the toxicity of these agents to normal cells.

The severity of neuroblastoma is particularly disturbing. Neuroblastoma tumors grow aggressively, metastasize, induce angiogenesis and remain resistant to multimodal therapy, demonstrating the need for development of novel therapeutic strategies that address efficient inhibition of cancer cells and eradication of any remaining refractory microscopic disease.

There is an urgent need to improve the outcome for patients with this disease, with an increased emphasis for the discovery of new drugs that are highly effective in eliminating aggressive cancer cells while also having insignificant toxicity toward normal cells.

Glioblastoma Multiforme (GBM)

Glioblastoma is the most common and most aggressive type of primary brain tumor in humans, involving glial cells and accounting for 52% of all parenchymal brain tumor cases and 20% of all intracranial tumors. Despite being the most prevalent form of primary brain tumor, GBMs occur in only 2-3 cases per 100,000 people in Europe and North America. According to the WHO classification of the tumors of the central nervous system, the standard name for this brain tumor is "glioblastoma"; it presents two variants: giant cell glioblastoma and gliosarcoma. Glioblastomas are also an important brain tumor of the canine, and research is ongoing to use this as a model for developing treatments in humans.

Treatment can involve chemotherapy, radiation, radiosurgery, corticosteroids, antiangiogenic therapy, and surgery. Glioblastoma has a very poor prognosis, despite multimodality treatment consisting of open craniotomy with surgical resection of as much of the tumor as possible, followed by concurrent or sequential chemoradiotherapy, antiangiogenic therapy with bevacizumab, gamma knife radiosurgery, and symptomatic care with corticosteroids. Other than the brainstem gliomas, it has the worst prognosis of any CNS malignancy.

Although common symptoms of the disease include seizure, nausea and vomiting, headache, and hemiparesis, the single most prevalent symptom is a progressive memory, personality, or neurological deficit due to temporal and frontal lobe involvement. The kind of symptoms produced depends highly on the location of the tumor, more so than on its pathological properties. The tumor can start producing symptoms quickly, but occasionally is an asymptomatic condition until it reaches an enormous size.

It is very difficult to treat glioblastoma due to several complicating factors: The tumor cells are very resistant to other conventional therapies, the brain is susceptible to damage due to conventional therapy, the brain has a very limited capacity to repair itself and many drugs cannot cross the blood-brain barrier to act on the tumor. Treatment of primary brain tumors and brain metastases consists of both symptomatic and palliative therapies. Supportive treatment focuses on relieving symptoms and improving the patient's neurologic function. The primary supportive agents are anticonvulsants and corticosteroids.

Historically, around 90% of patients with glioblastoma underwent anticonvulsant treatments, although it has been estimated that only approximately 40% of patients required this treatment. Recently, it has been recommended that neurosurgeons not administer anticonvulsants prophylactically, and should wait until a seizure occurs before prescribing this medication. Those receiving phenyloin concurrent with radiation may have serious skin reactions such as erythema multiforme and Stevens-Johnson syndrome. Dexamethasone given 4 to 10 mg every 4 to 6 h, can reduce peritumoral edema (through rearrangement of the blood-brain barrier) diminishing mass effect and lowering intracranial pressure with a decrease in headache or drowsiness.

Palliative treatment usually is conducted to improve quality of life and to achieve a longer survival time. It includes surgery, radiation therapy, and chemotherapy. A maximally feasible resection with maximal tumor-free margins is usually performed along with external beam radiation and chemotherapy. Gross total resection of tumor is associated with a better prognosis. Surgery is the first stage of treatment of glioblastoma. An average GBM tumor contains $10^{11}$ cells, which is on average reduced to $10^9$ cells after surgery. It is used to take a section for a pathological diagnosis, to remove some of the symptoms of a large mass pressing against the brain, to remove disease before secondary resistance to radiotherapy and chemotherapy, and to prolong survival.

Removal of 98% or more of the tumor has been associated with a significantly longer healthier time than if less than 98% of the tumor is removed. The chances of near-complete initial removal of the tumor can be greatly increased if the surgery is guided by a fluorescent dye known as 5-aminolevulinic acid. On average, radiotherapy after surgery can reduce the tumor size to $10^7$ cells. Whole brain radiotherapy does not improve when compared to the more precise and targeted three-dimensional conformal radiotherapy. A total radiation dose of 60-65 Gy is typical for treatment. Boron neutron capture therapy has been tested as an alternative treatment for glioblastoma multiforme but is not in common use.

The standard of care for glioblastoma includes chemotherapy during and after radiotherapy. On average, chemotherapy after surgery and radiotherapy can initially reduce the tumor size to $10^6$ cells. The use of temozolomide both during radiotherapy and for six months post radiotherapy results in a significant increase in median survival with minimal additional toxicity. This treatment regime is now standard for most cases of glioblastoma where the patient is not enrolled in a clinical trial. Temozolomide seems to work by sensitizing the tumor cells to radiation. The U.S. Food and Drug Administration approved Avastin (bevacizumab) to treat patients with glioblastoma at progression after standard therapy based on the results of 2 studies that showed Avastin reduced tumor size in some glioblastoma patients. In the first study, 28% of glioblastoma patients had tumor shrinkage, 38% survived for at least one year, and 43% survived for at least 6 months without their disease progressing.

Relapse of glioblastoma is attributed to the recurrence and persistence of tumor stem cells. In a small trial, a tumor B-cell hybridoma vaccine against tumor stem cells elicited a specific tumor immune reaction thus enhancing immune response to the disease. Larger trials are in progress to further assess this approach to treating glioblastoma. Long-term disease-free environment is possible, but the tumor usually reappears, often within 3 cm of the original site, and 10-20% may develop new lesions at distant sites.

Patients most fear the adverse effects of systemic chemotherapy when undergoing treatment for cancer. Nausea and vomiting are the most common and severe side effects. Other adverse side effects include cytopenia, infection, cachexia, mucositis in patients receiving high doses of chemotherapy with bone marrow rescue or radiation therapy; alopecia (hair loss); cutaneous complications (Abeloff, et al: *Alopecia and Cutaneous Complications.*, 755-756. In Abeloff, M. D., Armitage, J. O., Lichter, A. S., and Niederhuber, J. E. (eds) Clinical Oncology. Churchill Livingston, N.Y., 1992), such as pruritis, urticaria, and angioedema; neurological complications; pulmonary and cardiac complications in patients receiving radiation or chemotherapy; and reproductive and endocrine complications.

Chemotherapy-induced side effects significantly impact the quality of life of the patient and may dramatically influence patient compliance with treatment. Additionally, adverse side effects associated with chemotherapeutic agents are generally the major dose-limiting toxicity (DLT) in the administration of these drugs. For example, mucositis, is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe, may lead to hospitalization, or require treatment with analgesics for the treatment of pain. The adverse side effects induced by chemotherapeutic agents and radiation therapy have become of major importance to the clinical management of cancer patients.

Typically the subject is suffering from or at risk of suffering from a CNS tumor. Tumors of the CNS include but are not limited to cancers such as neuroblastoma and glioblastoma. Other types of central nervous system tumors include:

Neuroepithelial Tumors of the CNS
1. Astrocytic tumors [glial tumors—categories I-V, below—may also be subclassified as invasive or non-invasive, although this is not formally part of the WHO system, the non-invasive tumor types are indicated below. Categories in italics are also not recognized by the new WHO classification system, but are in common use.]
    1. Astrocytoma (WHO grade II)
        1. variants: protoplasmic, gemistocytic, fibrillary, mixed
    2. Anaplastic (malignant) astrocytoma (WHO grade III)
        1. hemispheric
        2. diencephalic
        3. optic
        4. brain stem
        5. cerebellar
    3. Glioblastoma multiforme (WHO grade IV)
        1. variants: giant cell glioblastoma, gliosarcoma
    4. Pilocytic astrocytoma [non-invasive, WHO grade I]
        1. hemispheric
        2. diencephalic
        3. optic
        4. brain stem
        5. cerebellar
        5. Subependymal giant cell astrocytoma [non-invasive, WHO grade I]
    6. Pleomorphic xanthoastrocytoma [non-invasive, WHO grade I]
2. Oligodendroglial tumors
    1. Oligodendroglioma (WHO grade II)
    2. Anaplastic (malignant) oligodendroglioma (WHO grade III)
3. Ependymal cell tumors
    1. Ependymoma (WHO grade II)
        1. variants: cellular, papillary, epithelial, clear cell, mixed
    2. Anaplastic ependymoma (WHO grade III)
    3. Myxopapillary ependymoma
    4. Subependymoma (WHO grade I)
4. Mixed gliomas
    1. Mixed oligoastrocytoma (WHO grade II)
    2. Anaplastic (malignant) oligoastrocytoma (WHO grade III)
    3. Others (e.g. ependymo-astrocytomas)
5. Neuroepithelial tumors of uncertain origin
    1. Polar spongioblastoma (WHO grade IV)
    2. Astroblastoma (WHO grade IV)
    3. Gliomatosis cerebri (WHO grade IV)
6. Tumors of the choroid plexus
    1. Choroid plexus papilloma
    2. Choroid plexus carcinoma (anaplastic choroid plexus papilloma)
7. Neuronal and mixed neuronal-glial tumors
    1. Gangliocytoma
    2. Dysplastic gangliocytoma of cerebellum (Lhermitte-Duclos)
    3. Ganglioglioma
    4. Anaplastic (malignant) ganglioglioma
    5. Desmoplastic infantile ganglioglioma
        1. desmoplastic infantile astrocytoma
    6. Central neurocytoma
    7. Dysembryoplastic neuroepithelial tumor
    8. Olfactory neuroblastoma (esthesioneuroblastoma)
        1. variant: olfactory neuroepithelioma
8. Pineal Parenchyma Tumors
    1. Pineocytoma
    2. Pineoblastoma
    3. Mixed pineocytoma/pineoblastoma
9. Tumors with neuroblastic or glioblastic elements (embryonal tumors)
    1. Medulloepithelioma
    2. Primitive neuroectodermal tumors with multipotent differentiation
        1. medulloblastoma
            1. variants: medullomyoblastoma, melanocytic medulloblastoma, desmoplastic medulloblastoma
        2. cerebral primitive neuroectodermal tumor
    3. Neuroblastoma
        1. variant: ganglioneuroblastoma
    4. Retinoblastoma
    5. Ependymoblastoma Other CNS Neoplasms
1. Tumors of the Sellar Region
    1. Pituitary adenoma
    2. Pituitary carcinoma
    3. Craniopharyngioma
2. Hematopoietic tumors
    1. Primary malignant lymphomas
    2. Plasmacytoma
    3. Granulocytic sarcoma
    4. Others
3. Germ Cell Tumors
    1. Germinoma
    2. Embryonal carcinoma
    3. Yolk sac tumor (endodermal sinus tumor)
    4. Choriocarcinoma
    5. Teratoma
    6. Mixed germ cell tumors
4. Tumors of the Meninges
    1. Meningioma
        1. variants: meningothelial, fibrous (fibroblastic), transitional (mixed), psammomatous, angiomatous, microcystic, secretory, clear cell, chordoid, lymphoplasmacyte-rich, and metaplastic subtypes
    2. Atypical meningioma
    3. Anaplastic (malignant) meningioma
5. Non-menigothelial tumors of the meninges
    1. Benign Mesenchymal
        1. osteocartilaginous tumors
        2. lipoma 3. fibrous histiocytoma
 4. others
2. Malignant Mesenchymal
 1. chondrosarcoma
 2. hemangiopericytoma
 3. rhabdomyosarcoma
 4. meningeal sarcomatosis
 5. others
3. Primary Melanocytic Lesions
 1. diffuse melanosis
 2. melanocytoma
 3. maliganant melanoma
  1. variant meningeal melanomatosis
4. Hemopoietic Neoplasms
 1. malignant lymphoma
 2. plasmactoma
 3. granulocytic sarcoma
5. Tumors of Uncertain Histogenesis
 1. hemangioblastoma (capillary hemangioblastoma)
6. Tumors of Cranial and Spinal Nerves
1. Schwannoma (neurinoma, neurilemoma)
 1. cellular, plexiform, and melanotic subtypes
2. Neurofibroma
 1. circumscribed (solitary) neurofibroma
 2. plexiform neurofibroma
3. Malignant peripheral nerve sheath tumor (Malignant schwannoma)
 1. epithelioid
 2. divergent mesenchymal or epithelial differentiation
 3. melanotic
7. Local Extensions from Regional Tumors
1. Paraganglioma (chemodectoma)
2. Chordoma
3. Chodroma
4. Chondrosarcoma
5. Carcinoma
8. Metastatic tumours
9. Unclassified Tumors
10. Cysts and Tumor-like Lesions
1. Rathke cleft cyst
2. Epidermoid
3. Dermoid
4. Colloid cyst of the third ventricle
5. Enterogenous cyst
6. Neuroglial cyst
7. Granular cell tumor (choristoma, pituicytoma)
8. hypothalamic neuronal hamartoma
9. nasal glial herterotopia
10. plasma cell granuloma Subjects can be any mammal, and are preferably human subjects. The subjects can be of any age, ranging from new born babies to fully grown adults.

In certain embodiments, the progesterone is administered to a subject not suffering from a hormone-related disorder, and in particular is typically not suffering from a breast, endometrial or ovarian cancer. In certain embodiments, the subject is not an adult, and typically can range in age from one to twenty-one years, or more typically less than eighteen, or even more typically less than thirteen years old. Typically, the subject has not completed puberty.

In one embodiment, treatment of the CNS tumor is provided by a single dose of a compound, while in another embodiment the treatment is provided by repeated exposure. In certain embodiments, the compound, typically progesterone, is administered at least one time per day for at least two, at least three, at least four, at least five, at least six, at least seven or more days. The steroid can also be administered less than one time a day, over the course of at least one week, or at least two weeks, or at least three weeks, or one month or more.

In certain embodiments, the steroid is given to a subject in combination or alternation with another compound, and in particular with a chemotherapeutic. The chemotherapeutic can include one or more drug selected from Carboplatin (Paraplat, Paraplatin), Cyclophosphamide (Cytoxan, Clafen, Neosar) and Doxorubicin (Adriamycin), Cyclophosphamide, Ifosfamide (Cyfos, Ifex, Ifosfamidum), Cisplatin (Platinol), Vincristine (Vincasar), Doxorubicin, Melphalan (Alkeran), Etoposide (VePesid, Toposar), Teniposide (Vumon) and Topotecan (Hycamtin).

In certain embodiments, the compound is administered in combination with another treatment selected from surgery to remove the tumor, radiation therapy, chemotherapy and bone marrow transplantation. In certain embodiments, the steroid is administered to a subject in combination or alternation with a cytotoxic agent (topotecan, a topoisomerase I inhibitor, cisplatin, doxorubicin and cyclophosphamides, either alone or in combination) retinoids (13-cis-RA, all-trans-RA and fenretinide), immunotherapy (anti-GD2 antibodies), cytokines (GM-CSF and IL2) radioiodinated meta-iodobenzylguanidine (to target delivery of radiotherapy).

In certain embodiments, the steroid is administered in a combination with other treatment consisting of open craniotomy with surgical resection of as much of the tumor as possible, followed by concurrent or sequential chemoradiotherapy, antiangiogenic therapy with bevacizumab, gamma knife radiosurgery, and symptomatic care with corticosteroids.

In certain embodiments, the steroid is administered in combination or alternation with temozolomide and radiotherapy or Avastin (bevacizumab).

Pharmaceutical Compositions

The compound or an analogue or derivative thereof may be used in conjunction with one or more additional compounds, in the treatment of the inhibition of CNS tumors. A compound of the present disclosure can be formulated as a pharmaceutical composition.

Such a composition can then be administered orally, parenterally, by inhalation spray, rectally, or topically in dosage unit formulations containing conventional nontoxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., Remington's Pharmaceutical Sciences, Mack Publishing Co., Easton, Pa.; 1975. Another example of includes Liberman, H. A. and Lachman, L., Eds., Pharmaceutical Dosage Forms, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the compound or an analogue or derivative thereof can be prepared by mixing the steroid or an analogue or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian subject treated and the particular mode of administration.

EXAMPLES

The following examples are provided as illustrations of the disclosure and to provide those of ordinary skill in the art with specific preferred methods within the scope of the present disclosure and are not intended to limit the scope of what the inventors regard as their disclosure.

Example 1

Figure 1C:
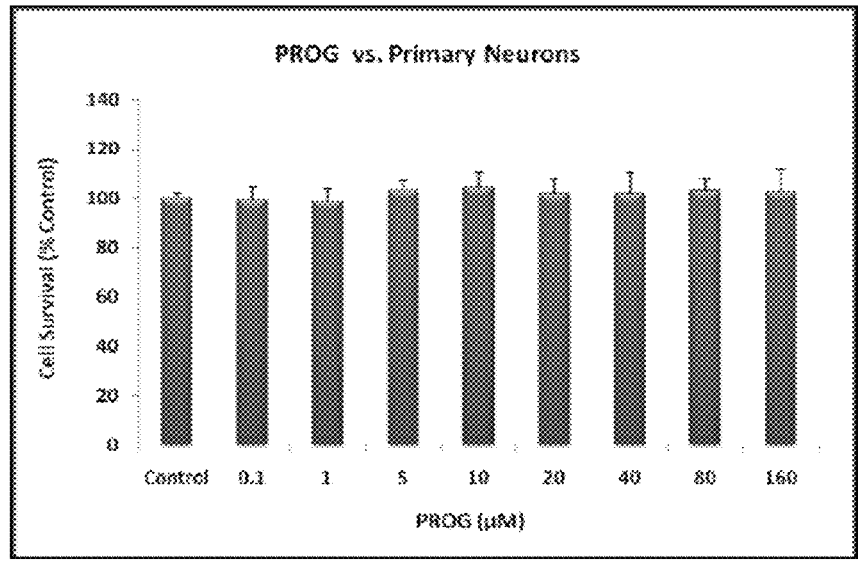

The Effect of a Single Exposure of Progesterone on the Survival of Human Neuroblastoma (SK-N-AS) Cells and Rat Primary Cortical Neurons is Provided The human neuroblastoma cells (SK-N-AS) were cultured in a DMEM medium and E18 rat primary cortical neurons were cultured for 8-10 days in Neurobasal medium. Cells were then exposed to different concentrations of progesterone (0.1, 1, 5, 10, 20, 80, 160 µM) for 48 hours and the medium was not changed until the end of the experiment. An MTT reduction assay was used to estimate cell viability. Progesterone induced a significant cell death ($P<0.05$) in SK-N-AS cells at 5 µM and 10 µM concentrations compared to the control group (FIG. 1A). Conversely, progesterone did not result in cell death in primary cortical neurons at any concentrations (FIG. 1C).

Example 2

Figure 2A:
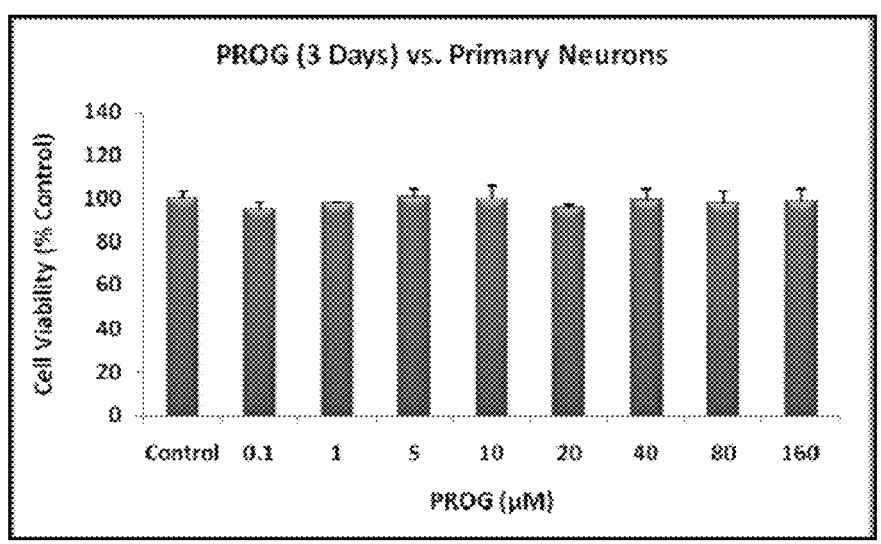
FIG. 2 shows the effect of repeated progesterone exposure (A,B: 3 days, C,D: 6 days) on the viability of human neuroblastoma (SK-N-AS) cells and primary cortical neurons (MTT assay). Analysis of variance (ANOVA) followed by a Dunnett test was used to compare treatment groups to controls. The significance of results was set at P<0.05 when compared to controls. Values were expressed as means±SD of three experiments.
Figure 2B:
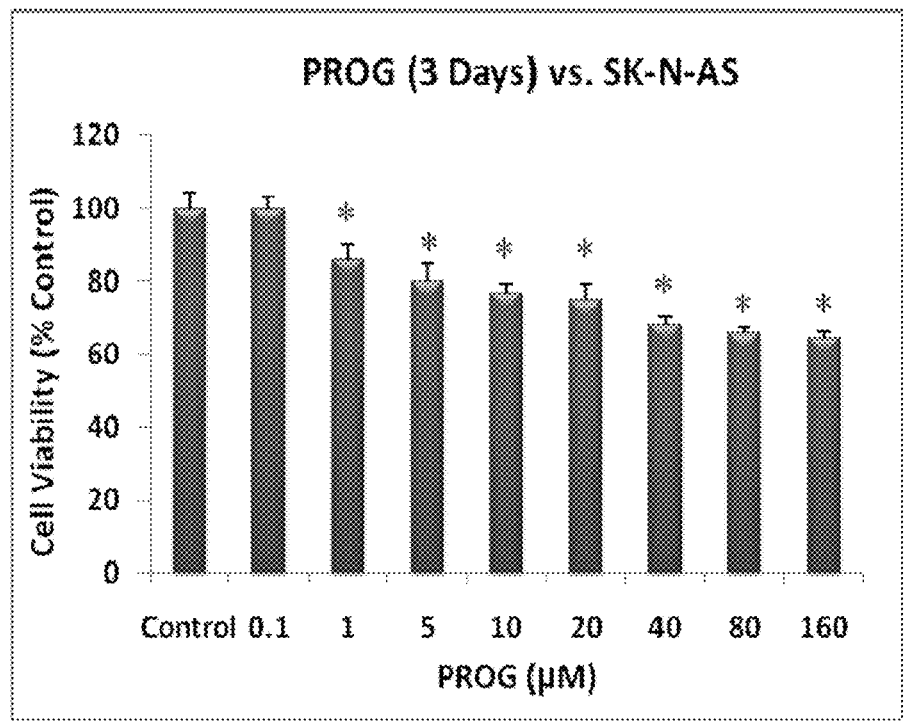
Figure 2C:
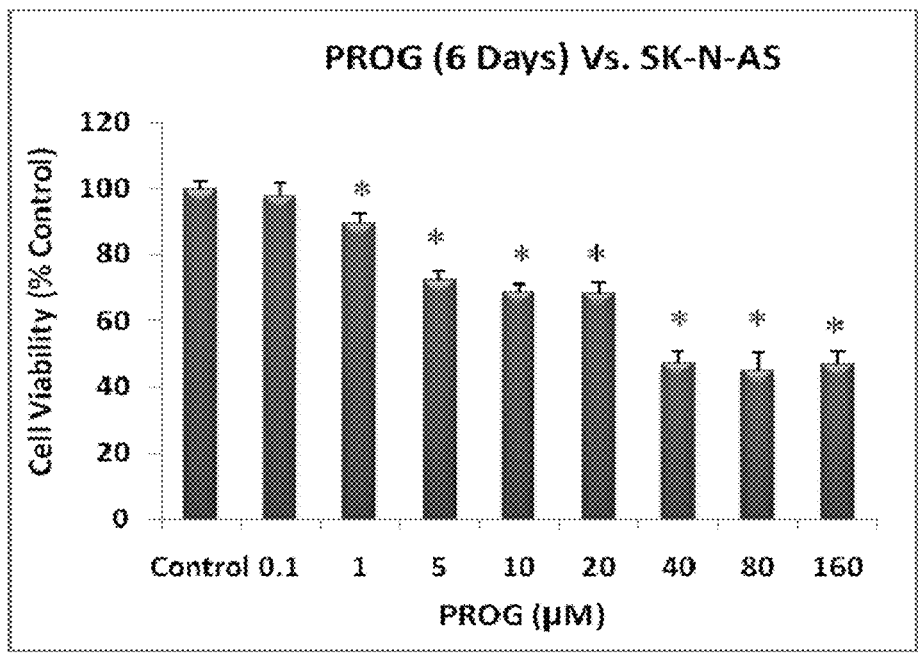
Figure 2D:
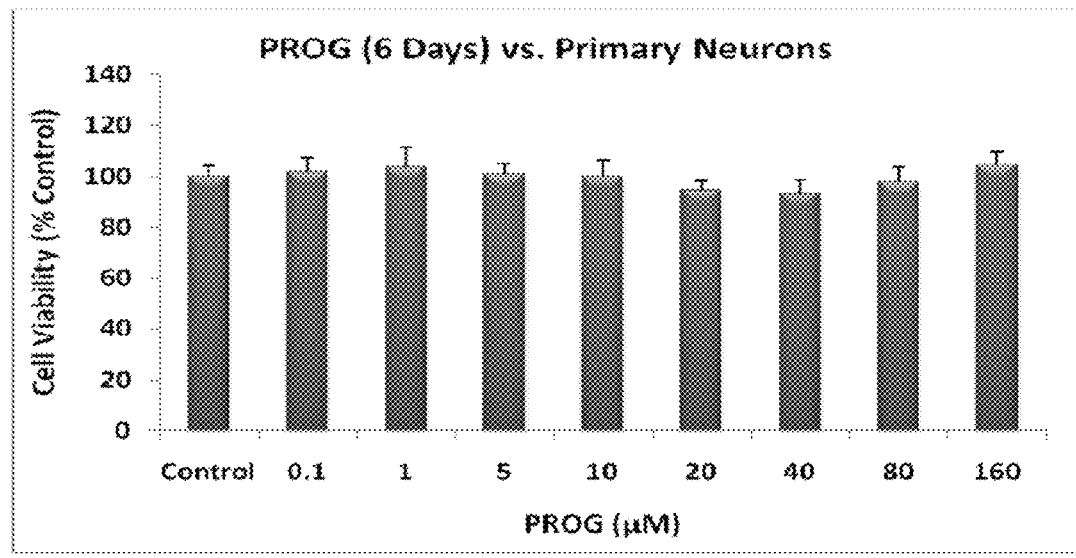

The Effect of Repeated Exposure of Progesterone, for 3 and 6 Days, in the Survival of Human Neuroblastoma (SK-N-AS) Cells and Rat Primary Cortical Neurons is Provided In order to evaluate the effect of repeated exposure of progesterone on the survival of primary neurons and neuroblastoma cells, E18 rat primary cortical neurons were cultured for 8-10 days in Neurobasal medium and SK-N-AS cells were used for experiments when they reached 80% confluence in DMEM medium. Cells were exposed to different concentrations of progesterone (0.1, 1, 5, 10, 20, 80, 160 µM) daily for 3 days and 6 days by replacing new culture medium containing different concentrations of progesterone. Progesterone exposure for 3 days caused significant ($P<0.05$) cell death in a concentration dependant manner in SK-N-AS cells (FIG. 2A) but no death in primary cortical neurons (FIG. 2B). As a result of repeated progesterone exposure for 6 days, cell death ($P<0.05$) was observed in SK-N-AS cells in a concentration dependant manner (FIG. 2C). No cell death was observed in primary cortical neurons after 6 days of progesterone exposure (FIG. 2D).

Example 3

Figure 3:
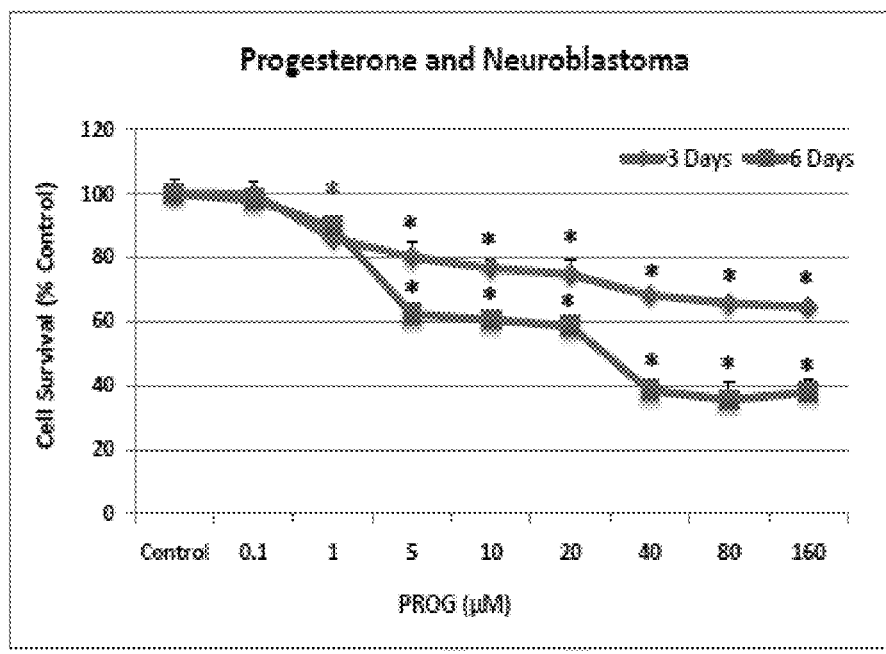
FIG. 3 show the effects of PROG exposure for 3 and 6 days on the viability of Neuroblastoma cells (SK-N-AS). Cells were exposed to different concentrations of PROG (0.1, 1, 5, 10, 20, 80, 160 µM) daily for 3 days and 6 days. The statistical analysis of data was performed with analysis of variance (ANOVA) followed by Dunnett test to compare several treatment group to a single control group. The significance of results was set at P<0.05. Values are expressed as Means±SD of three experiments. Significant difference *P<0.05 when compared to control.

The Effect of Repeated Exposure of Progesterone, for 3 Days and 6 Days, on the Survival of Two Different Human Glioblastoma Cell Lines (Glioblastoma-1: U87MG and Glioblastoma-2: U87dEGFR) is Provided We tested the efficacy of repeated exposure to progesterone treatment on the viability of two human glioblastoma cell lines, U87MG and U87dEGFR. High doses of progesterone killed both glioblastoma cell lines in a dose dependant manner. Six days of progesterone treatment was more effective than 3 days (FIG. 3).

Example 4

Figure 4:
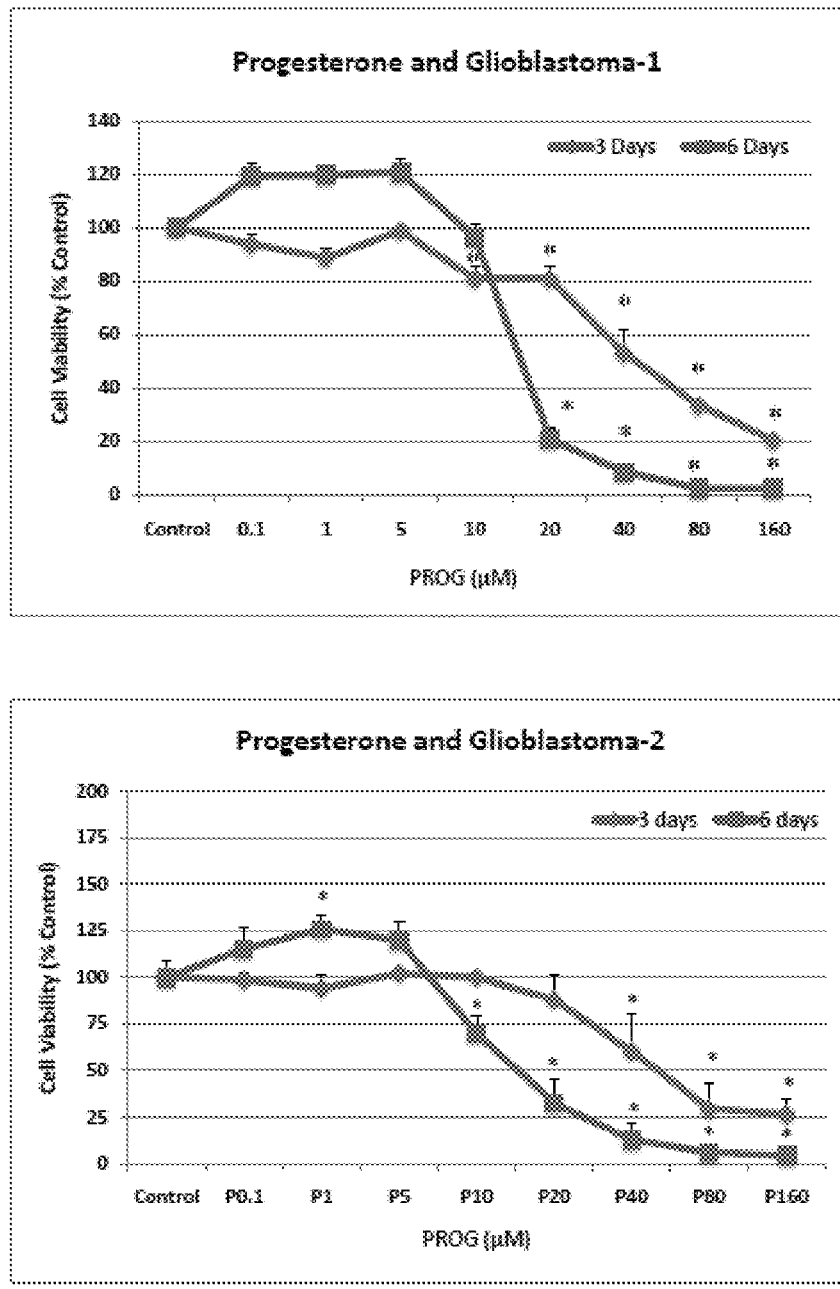
FIG. 4 shows the effects of Progesterone's (PROG) repeated exposure on the viability of glioblastoma 1 (U87MG) cells and glioblastoma 2 (U87dEGFR) cells. Cells were exposed to different concentrations of PROG daily for 3 days and 6 days by replacing culture medium containing PROG. The stock solution of PROG was prepared in DMSO (Final concentration: <5 µl/ml medium). Data were analyzed using analysis of variance (ANOVA) followed by Dunnett's test. Values are expressed as Means±SD of two independent experiments with duplicate samples. Significant difference *P<0.05 when compared to control values.

The Effect of Progesterone Treatment on the Morphology of Glioblastoma Cell Line U87MG is Shown The changes in the morphology of U87MG glioblastoma cell line after exposure to different concentrations of progesterone are shown in FIG. 4. The characteristics of healthy cells can be seen in the control group as elongated cells with long processes. A marked change can be seen with the increasing concentrations of progesterone in the glioblastoma groups. At high concentrations (40, 80 and 160 µM), cells seem to lose their original shape, become detached from the surface, and eventually die.

Example 5

Figure 5:
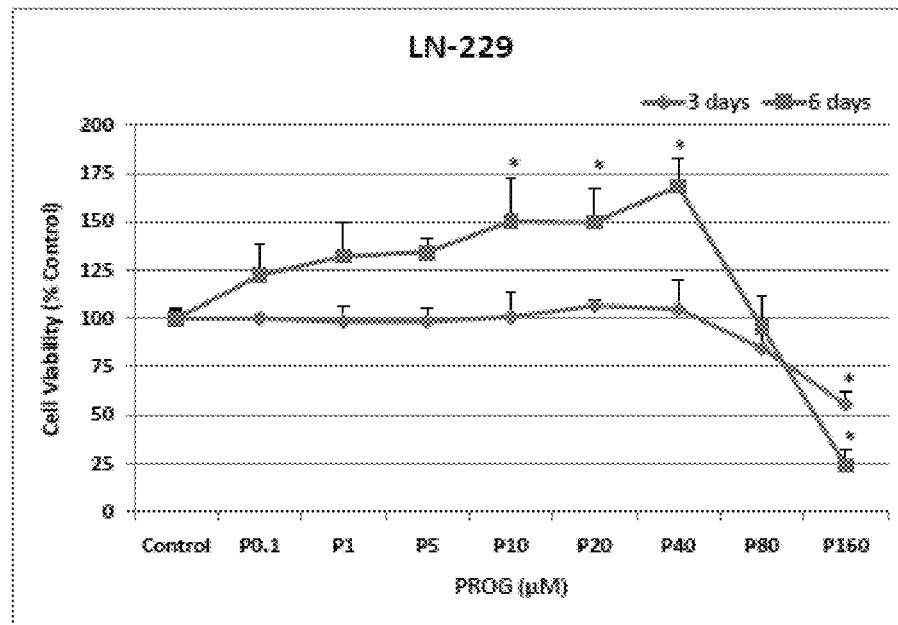
FIG. 5 shows the effects of Progesterone's (PROG) repeated exposure on the viability of glioblastoma (LN-229) cells. Cells were exposed to different concentrations of PROG daily for 3 days and 6 days by replacing culture medium containing PROG. The stock solution of PROG was prepared in DMSO (Final concentration: <5 µl/ml medium). Data were analyzed using analysis of variance (ANOVA) followed by Dunnett's test. Values are expressed as Means±SD of two independent experiments with duplicate samples. Significant difference *P<0.05 when compared to control values.
Figure 6:
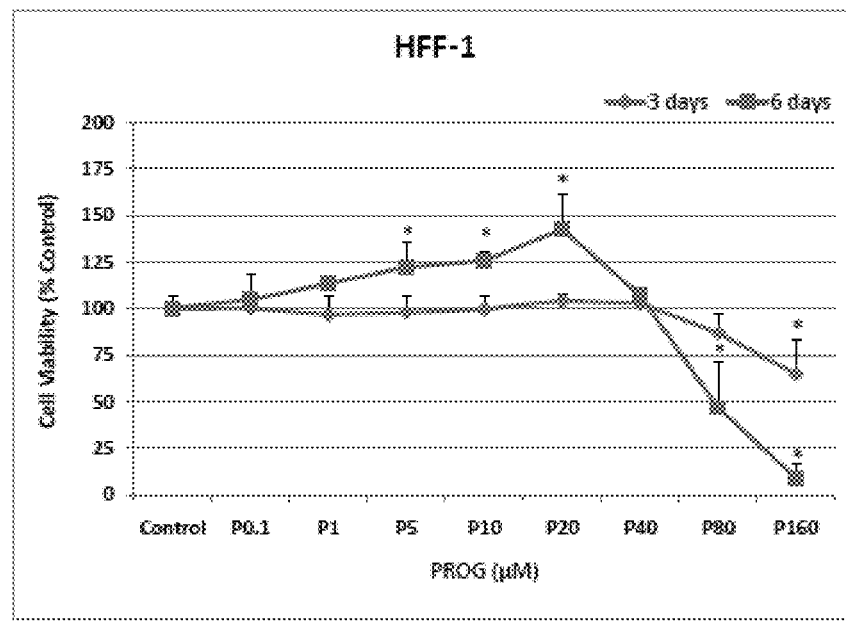
FIG. 6 shows the effects of Progesterone's (PROG) repeated exposure on the viability of a primary fibroblasts (HFF-1) cell line. Cells were exposed to different concentrations of PROG daily for 3 days and 6 days by replacing culture medium containing PROG. The stock solution of PROG was prepared in DMSO (Final concentration: <5 µl/ml medium). Data were analyzed using analysis of variance (ANOVA) followed by Dunnett's test. Values are expressed as Means±SD of two independent experiments with duplicate samples. Significant difference *P<0.05 when compared to control values
Figure 7:
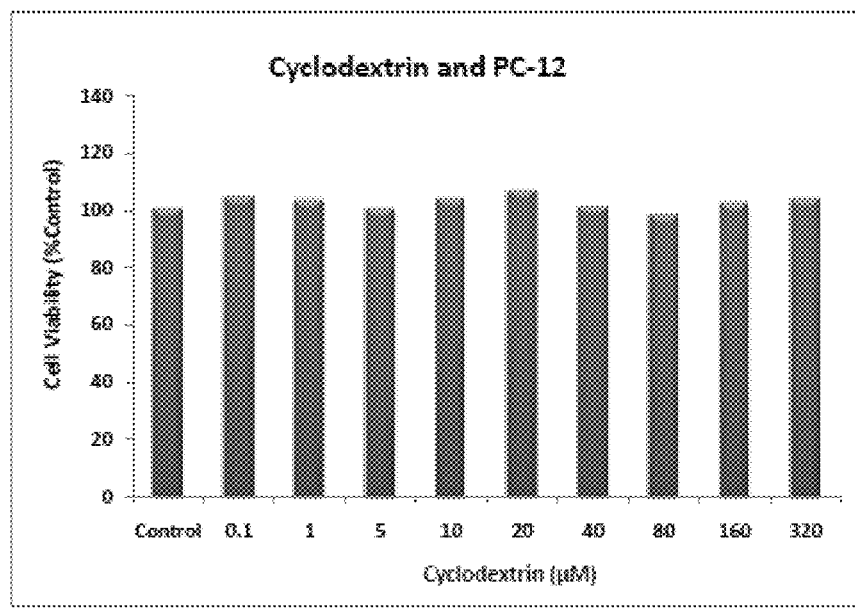
FIG. 7 shows data on how cyclodextrin affects survival of PC-12 cells. PC-12 cells were treated with different concentrations of cyclodextrin for 48 h. The values are expressed as mean±SD of duplicate samples. This experiment was done to answer the question if any compound can kill tumor cells at high doses. B-Cyclodextrin is an inert compound and used as a vehicle for Progesterone. We observed that even at very high concentration (320 uM) it could not induce cell death. These findings strongly suggest the anti-tumor efficacy of Progesterone.
Figure 8:
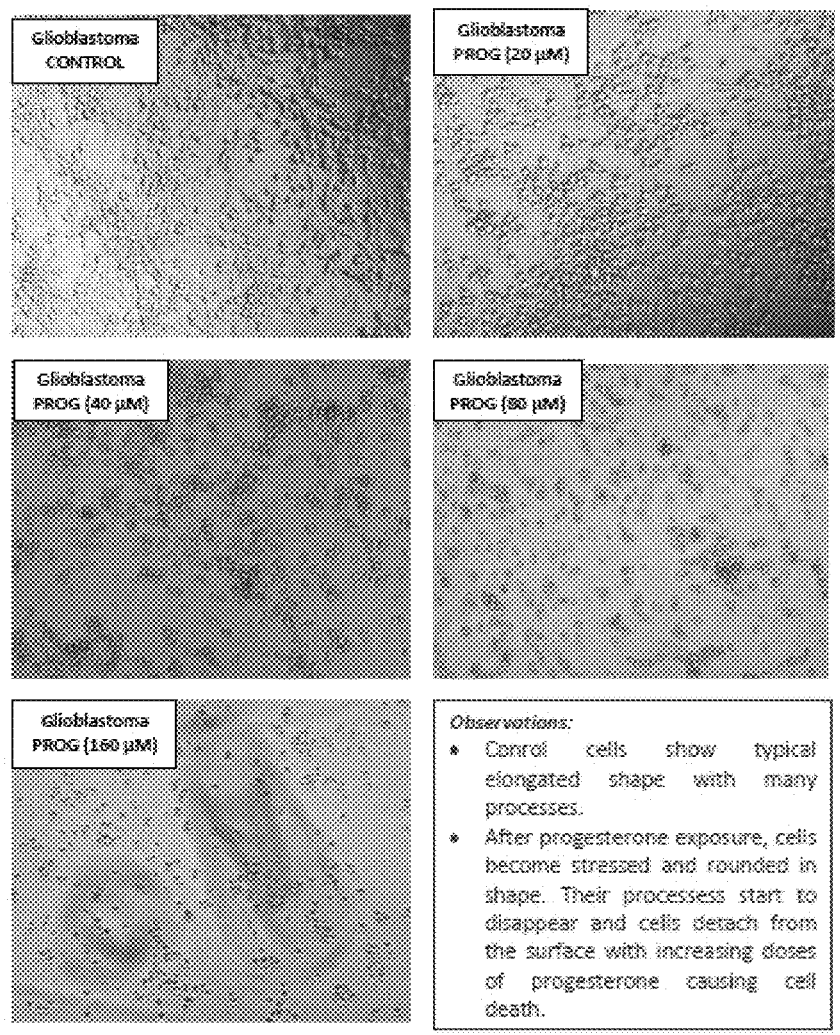
FIG. 8 depicts the morphological changes in glioblastoma cells after exposure to different doses of progesterone, using a phase contrast microscope.
Figure 9:
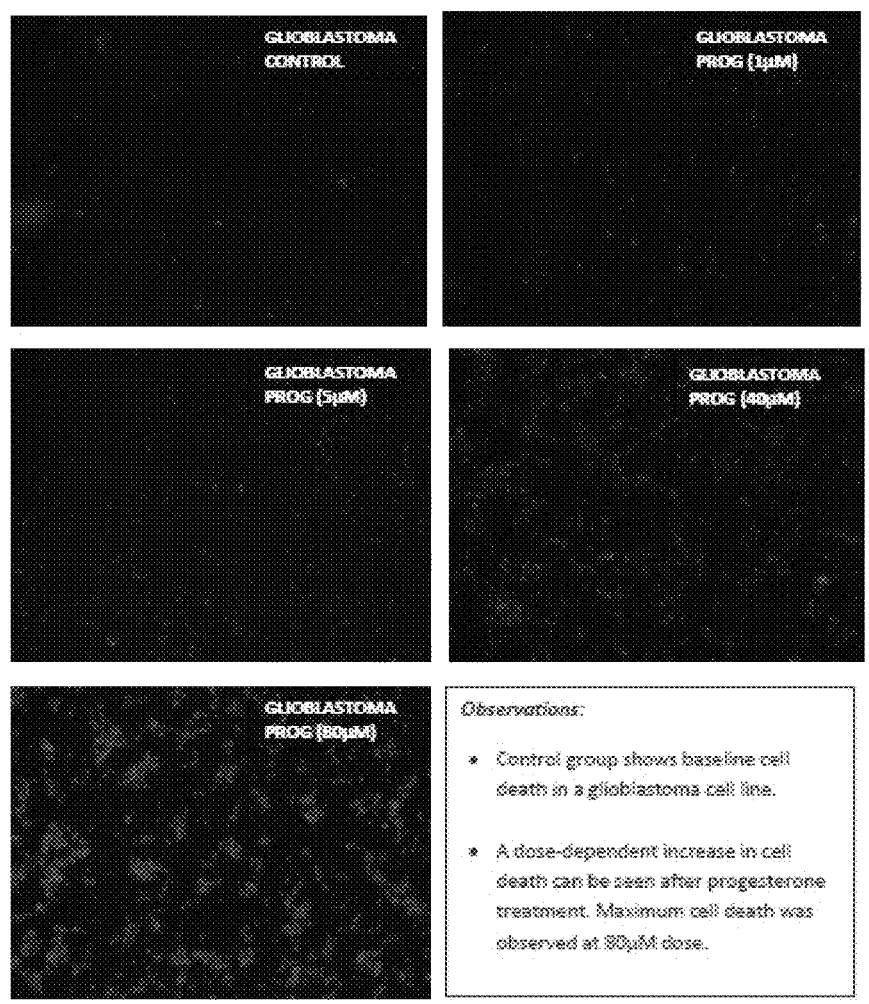
FIG. 9: Representative photomicrographs of Propidium Iodide (PI) staining in GLIOBLASTOMA (U87dEGFR) cell-line after PROG exposure.
Figure 10:
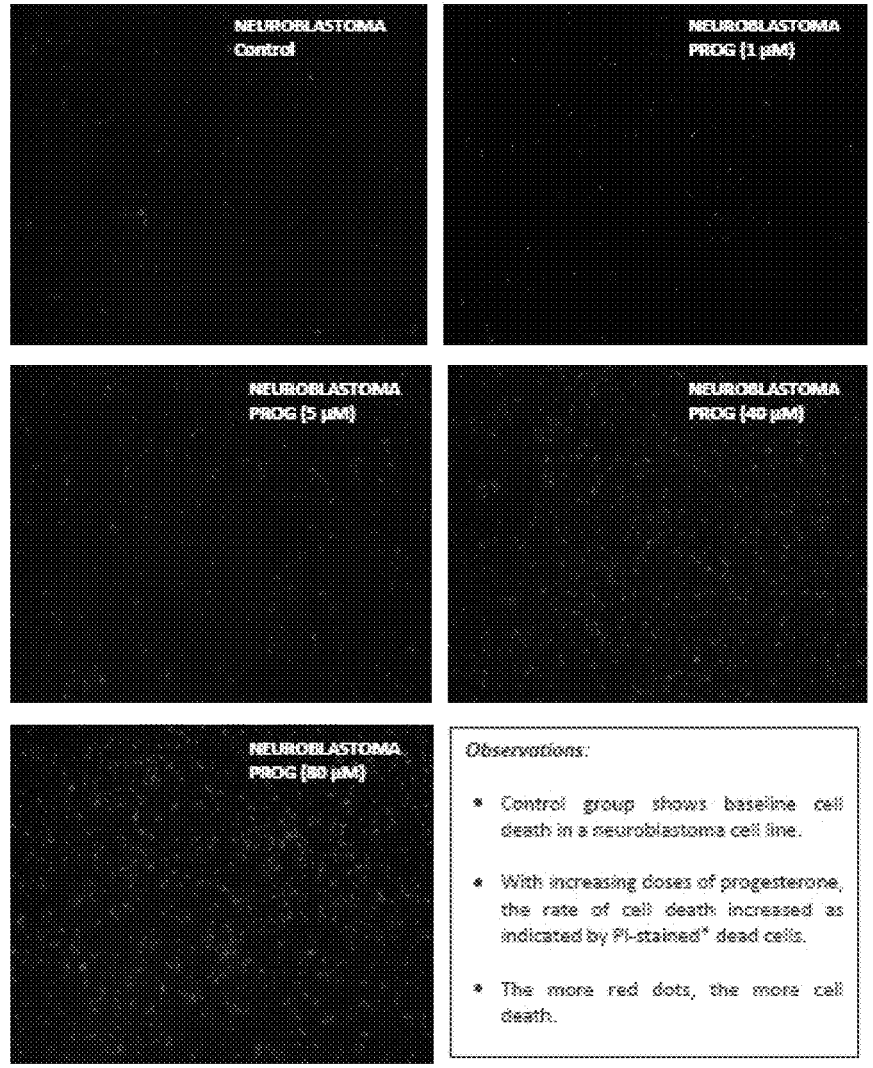
FIG. 10 shows representative photomicrographs of Propidium Iodide (PI)-staining in Neuroblastoma (SK-N-AS) cells after PROG exposure.
Figure 11:
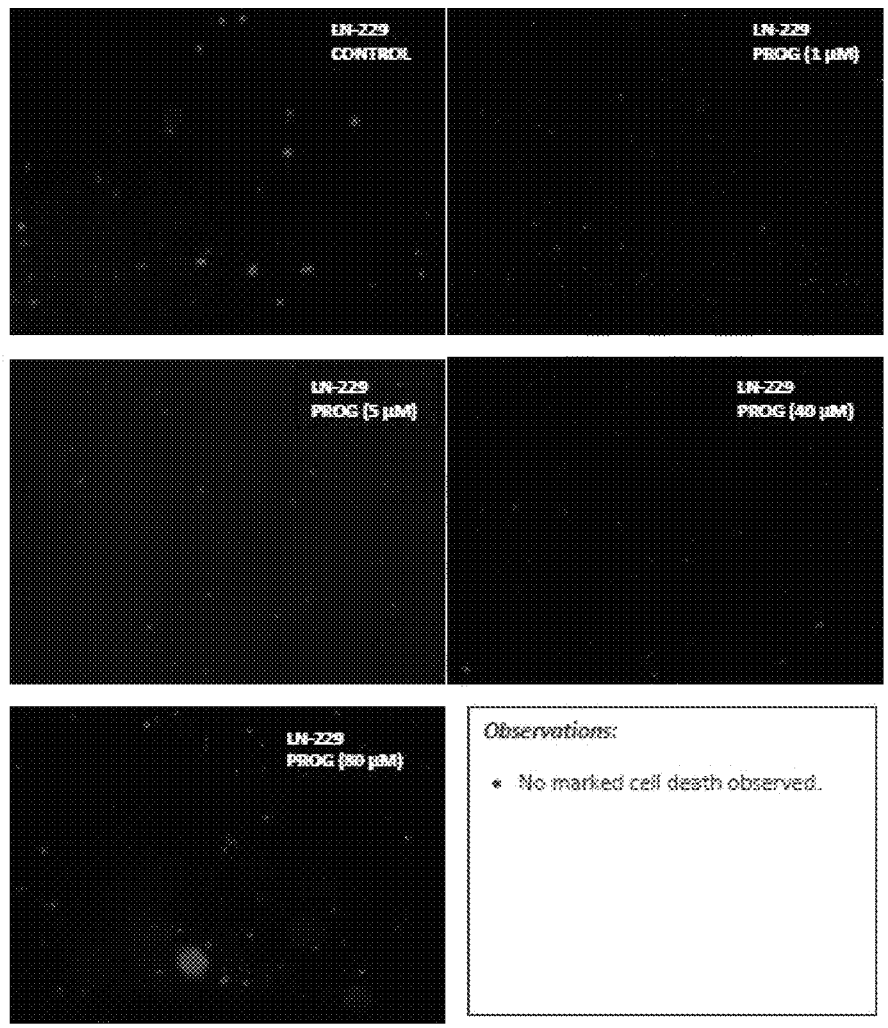
FIG. 11 shows representative photomicrographs of Propidium Iodide (PI) staining in GLIOBLASTOMA (LN-229) cell-line after 3 days of PROG's repeated exposure.
Figure 12:
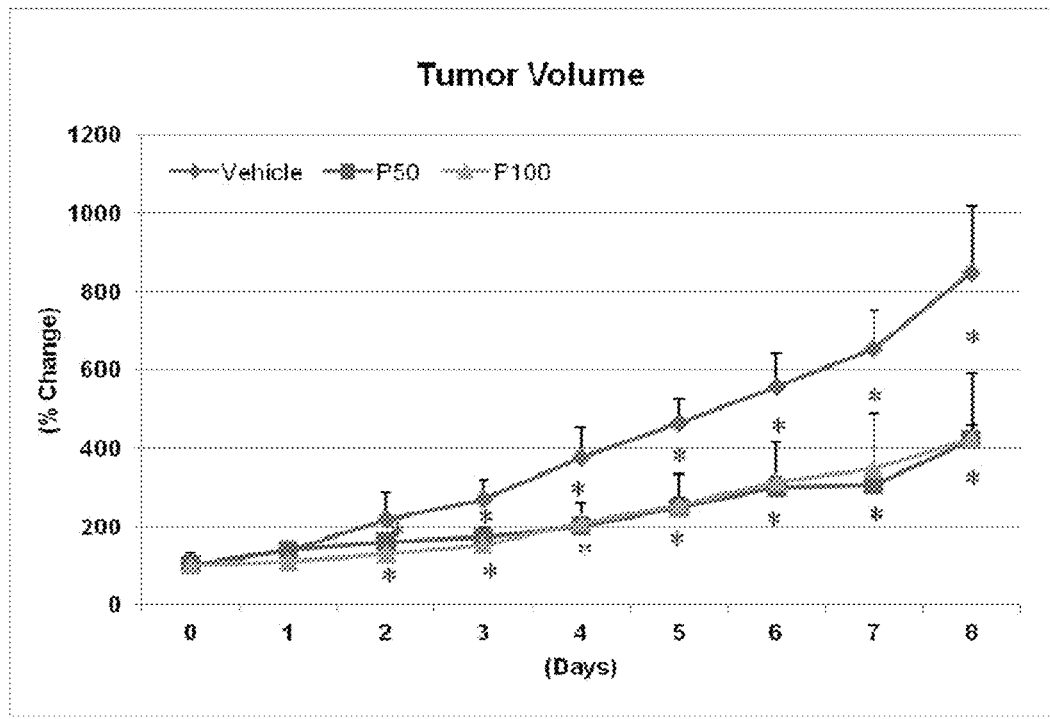
FIG. 12 shows the therapeutic effect of progesterone on the rate of tumor growth in a mouse xenograph model of neuroblastoma. The female nude mice were randomly divided into groups: progesterone (50 mg/kg, n=6); progesterone (100 mg/kg, n=6) and vehicle (n=5). Peritumoral injections of the two different doses of the progesterone injections (50 and 100 mg/kg) in saline were given daily for 8 days. The vehicle group received saline only. Data were normalized to the baseline values (day 1) and expressed as percent change in daily tumor growth.
Figure 13:
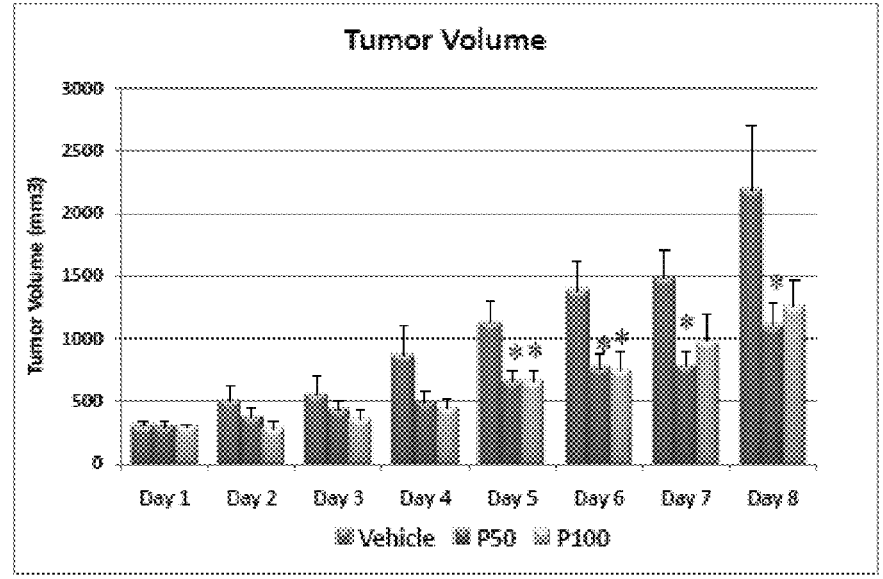
FIG. 13 shows the therapeutic effect of progesterone treatment on the tumor volume in a mouse xenograph model of neuroblastoma. Female nude mice were randomly divided into groups: progesterone (50 mg/kg, n=6); progesterone (100 mg/kg, n=6) and vehicle (n=5). Peritumor injections of two different doses of progesterone suspension (50 and 100 mg/kg) in saline were given daily for 8 days. The vehicle group received saline only. Values are expressed as mean tumor size for the different animals in each group. The significance of results was set at P<0.05 two-tailed. Values are expressed as % change in Means±SEM of tumor volume in different groups. Significant difference *P<0.05 compared to vehicle group.
Figure 14:
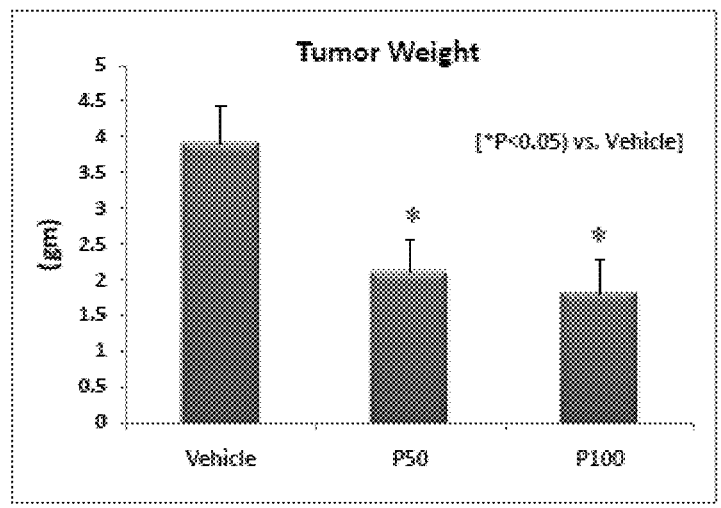
FIG. 14 shows data on the tumor weight in different groups. Data were analyzed using t-test. Significant difference *P<0.001 compared to vehicle. Values are expressed as Means±SEM.
Figure 15:
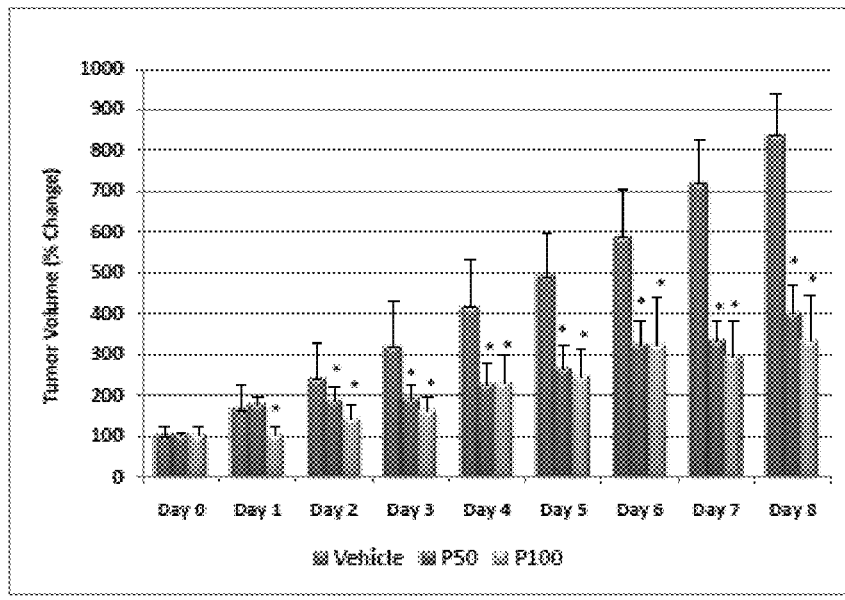
FIG. 15 shows data on tumor volume following the PROG treatment. Data were analyzed using one way analysis of variance (ANOVA) followed by Dunnett's test. Values are expressed as % change in Means±SEM of tumor volume in different groups. Significant difference *P<0.05 compared to vehicle group.
Figure 16:
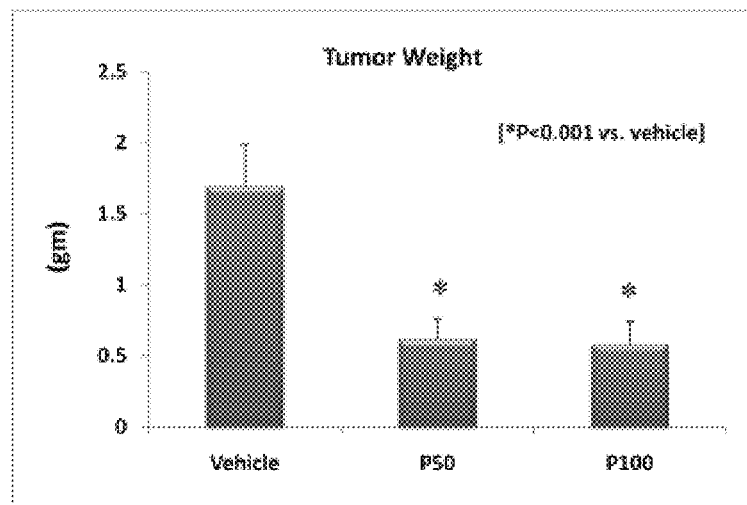
FIG. 16 shows data on tumor weight in different groups. Data were analyzed using t-test. Significant difference *P<0.001 compared to vehicle. Values are expressed as Means±SEM.
Figure 17:
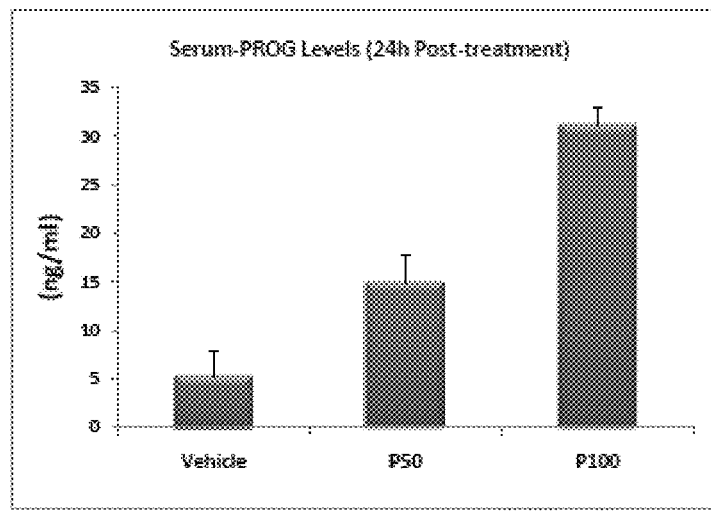
FIG. 17 shows data on bioavailability or Serum-PROG levels in different groups. Blood was collected 24 h Post-treatment. Progesterone levels were measured by RIA method. Values are expressed as Means±SD.
Figure 18:
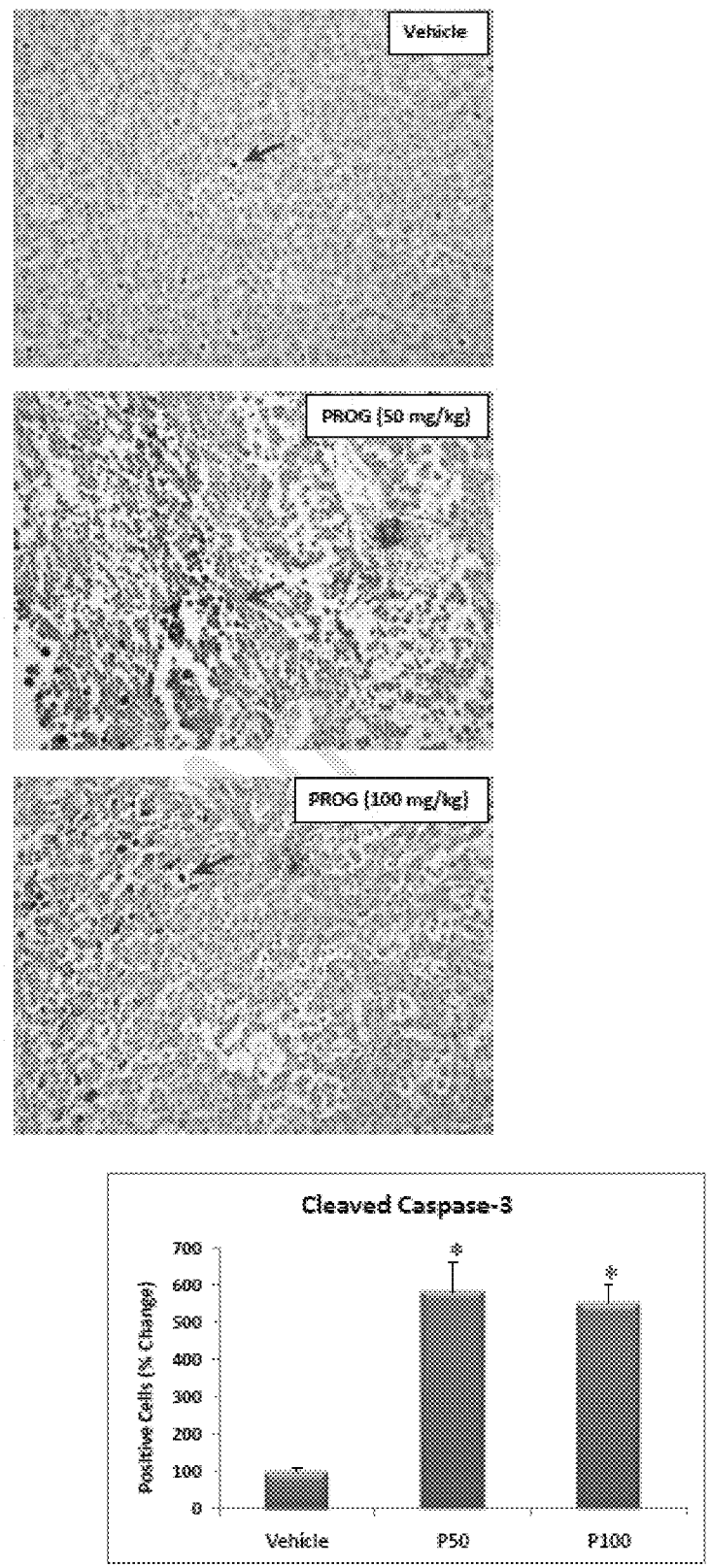
FIG. 18 shows date on [A] representative photomicrographs (40x) of immunohistochemistry for cleaved caspase-3 (marker of apoptosis) in paraffin embedded and DAB-stained tumor sections. The arrow indicates brown apoptotic cells. [B]: Cell counting in different groups. Values are expressed Means±SEM of % change in positive cells. Data were analyzed using two-tailed t-test. Significant difference *P<0.001 compared to vehicle.
Figure 19:
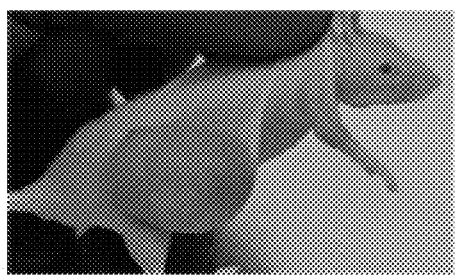
FIG. 19 is the representative photographs of mice from different groups on the eighth day of progesterone treatment. The photos represent the mean size of the tumors found in each of the three groups.
Figure 19:
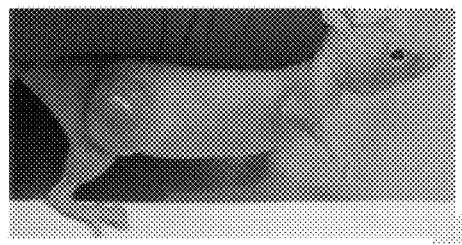
Figure 19:
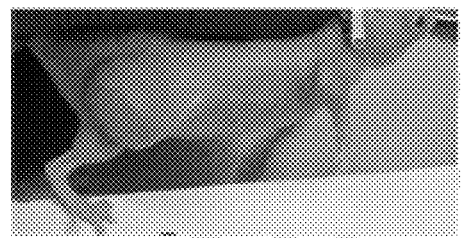

The Reduction in the Rate of Neuroblastoma Tumor Growth in Live Mice by Treatment with Progesterone is Shown The chemotherapeutic effects of progesterone in a mouse xenograft model of human neuroblastoma using a human cell line in female athymic nude mice (Hsd: Athymic Nude-Foxn1$^{nu}$). Tumors were allowed to grow to ~200 to 250 mm$^3$ and mice were divided into groups. Progesterone was given either at 50 mg/kg or 100 mg/kg as a peritumoral injection (one injection daily). This regimen was planned to be continued for up to two weeks to examine maximum tumor burden. All treated animals are being compared to appropriate controls for analysis of rate of daily tumor growth, tumor volume and regression. Toxicity is being assessed daily by survival, activity and body weight. We have thus far analyzed rate of growth after 8 days of treatment and found that the rate of tumor growth is reduced by almost 50% in both groups of progesterone treated animals compared to those given just saline vehicles (FIGS. 5 and 6), demonstrating a profound effect on tumor development. The representative photographs of the mice from the different groups on the 8$^{th}$ day of the progesterone treatment are shown in FIG. 7. They represent the mean size of the tumors found in each of the three groups.

The invention claimed is:

1. A method for treating neuroblastoma comprising administering a therapeutically-effective amount of progesterone or salt thereof to a subject in need thereof.

2. The method of claim 1, wherein the subject is a human patient.

3. The method of claim 1, wherein the subject is diagnosed with a neuroblastoma tumor.

4. The method of claim 1, wherein administration of progesterone or salt thereof can induce cell death in human neuroblastoma cells, while having no detrimental effect on primary cortical neurons.

5. The method of claim 1, wherein the subject is a human and is administered more than 50, 100, 200, 300 or 400 mg of progesterone or salt thereof daily.

6. The method of claim 1, wherein progesterone or salt thereof is administered in combination with a second chemotherapeutic agent.

* * * * *